United States Patent [19]

Turecek

[11] Patent Number: 5,792,623
[45] Date of Patent: Aug. 11, 1998

[54] METHOD FOR PRODUCING ACTIVATED BLOOD FACTORS WITH A PROTEASE AND A DETERGENT

[75] Inventor: Peter Turecek, Vienna, Austria

[73] Assignee: Immuno Aktiengesellschaft, Vienna, Austria

[21] Appl. No.: 482,399

[22] Filed: Jun. 7, 1995

Related U.S. Application Data

[63] Continuation-in-part of Ser. No. 40,261, Mar. 30, 1993, Pat. No. 5,432,062.

[30] Foreign Application Priority Data

Apr. 6, 1992 [AT] Austria .................................. A712/92

[51] Int. Cl.$^6$ .............................. C12P 21/06; C12N 9/74; A61K 38/48
[52] U.S. Cl. .................. 435/68.1; 435/214; 424/94.64
[58] Field of Search ................................ 435/68.1, 214; 424/94.64

[56] References Cited

U.S. PATENT DOCUMENTS

| | | | |
|---|---|---|---|
| 2,495,298 | 1/1950 | Szent-Gyorgy et al. | 435/214 |
| 4,210,580 | 7/1980 | Amrani | 530/383 |
| 4,380,511 | 4/1983 | Mannizza et al. | 435/214 |
| 4,470,969 | 9/1984 | Pancam et al. | 530/381 |
| 4,703,001 | 10/1987 | Vodian et al. | 435/5 |
| 5,143,838 | 9/1992 | Kraus et al. | 435/214 |
| 5,151,355 | 9/1992 | Crawley et al. | 435/214 |
| 5,158,873 | 10/1992 | Abbott et al. | 435/26 |
| 5,200,340 | 4/1993 | Foster et al. | 424/94.64 |
| 5,304,372 | 4/1994 | Michalski et al. | 435/94.64 |
| 5,354,682 | 10/1994 | Kingdom et al. | 435/214 |
| 5,432,062 | 7/1995 | Turecek | 435/68.1 |

FOREIGN PATENT DOCUMENTS

| | | |
|---|---|---|
| 20457/92 | 2/1993 | Australia . |
| 0 328 229 | 8/1989 | European Pat. Off. . |
| 0 369817 | 5/1990 | European Pat. Off. . |
| 443724 | 8/1991 | European Pat. Off. . |
| 3834550 | 4/1990 | Germany . |
| WO 93/07276 | 4/1993 | WIPO . |

OTHER PUBLICATIONS

Brosstad et al. "Preparation of Fibrin Monomers from Human Fibrinogon in Urea, Using Soluble or Insolubilized Thrombin," *Haemostasis* 6:225–235 (1977).

Kruithof et al. "Influence of Detergents on the Measurement of the Fibrinolytic Activity of Plasminogen Activators," *Thrombosis Research* 28:251–260 (1982).

Mann et al. "Multiple Active Forms of Thrombin," *The Journal of Biological Chemistry* 246(19):6106–6114 (Oct. 10, 1971).

Soulier et al. "Action De Divers 'Adsorbants' Sur Les Facteurs De Coagulation," *Novelle Revue Française d'Hematologie* 16(2):195–211 (1975).

Van Kley "Effect of Chaotropic Anions on the Activity of Arthrobacter Proteinase," *Federation Proceedings* 38(3):835 (1979).

Van Kley et al., "Alterations of Activity of Pancreatic Proteinases by Detergents," *Federation Proceedings* 41(3):763 (1982).

Landaburu et al. American Journal of Physiology 201(2): 298–302 (Aug. 1961).

Neugebauer (1987) "A Guide to the Properties and Uses of Detergents in Biology and Biochemistry", Published by Hoechst Celanese Corporation, pp. 4–7 and 24.

Stroud (1974) "Science America", vol. 231(1), pp. 74–88.

Neurath (1984) "Science America", vol. 224, pp. 350–357.

Esmon (1987) "Science America", vol. 235, pp. 1348–1352.

Sawyer et al. (1993) "J. Biol. Chem.", 248(24), pp. 8429–8433.

*Primary Examiner*—Jon P. Weber
*Attorney, Agent, or Firm*—Foley & Lardner

[57] ABSTRACT

Proenzymes or proforms of blood factors can be cleaved in the presence of a detergent or a chaotropic substance to produce active blood factors selected from the group consisting of Factor Va, Factor VIIa, Factor VIIIa, Factor IXa, Factor Xa, Factor XIa, Factor XIIa, Factor XIIIa and activated protein C. The chaotropic substance can be urea, guanidinium hydrochloride or a thiocyanate salt. Under these conditions, proteolytic activation occurs in a controlled and restricted manner. Consequently, it is possible to isolate high yields of active blood factor, while minimizing the production of inactive degradation products. Immobilization of the proenzyme or proform on a solid support prior to activation facilitates the separation of active blood factor from the proenzyme or proform and inactive peptide fragments.

13 Claims, 3 Drawing Sheets

METHOD FOR PRODUCING ACTIVATED BLOOD FACTORS WITH A PROTEASE AND A DETERGENT

CROSS-REFERENCE TO RELATED APPLICATIONS

This is a continuation-in-part of Ser. No. 08/040,261, filed on Mar. 30, 1993, now U.S. Pat. No. 5,432,062, which is incorporated by reference in its entirety.

BACKGROUND OF THE INVENTION

The present invention relates to a method for controlled proteolysis. More particularly, the invention concerns a method for obtaining enzymes by the proteolytic cleavage of proenzymes or proforms of blood coagulation factors in the presence of a detergent or a chaotropic substance.

Methods for producing enzymes from proenzymes are known to those of skill in the art. As an illustration, thrombin can be obtained by isolating prothrombin from plasma, adsorbing prothrombin on a solid carrier, such as methacrylic and acrylic copolymers, and by treating the adsorbate with plasma-derived proteases and $Ca^{2+}$ ions to release thrombin from the adsorbate. See, for example EP-A-0 378 798.

While trypsin also can be used to cleave prothrombin, under standard conditions trypsin digestion may degrade prothrombin to fragments of low molecular weight, leading to a complete loss of thrombin activity. *Biochim. Biophys. Act.* 329: 221 (1973).

These methods provide various prothrombin cleavage products, depending upon particular protease and treatment conditions. Such cleavage products may be used for therapy (e.g. thrombin), for diagnosis, or for the production of specific antibodies against the protein fragments. Since all known cleavage methods lead to a plurality of fragments, the preparation of the cleavage product for therapy or diagnosis is very labor-intensive. A further disadvantage of these multi-stage and time-consuming purification methods is that they necessarily involve high losses of yield.

SUMMARY OF THE INVENTION

Accordingly, it is an object of the present invention to provide an improved method for recovering enzymes or fragments from proteins.

It is a further object of this invention to provide a method for producing active blood coagulation factors.

These and other objects are achieved, in accordance with one embodiment of the present invention, by the provision of a method of proteolytically cleaving a proenzyme or proform of a blood coagulation factor comprising the step of incubating the proenzyme or proform with a protease in the presence of a detergent or a chaotropic substance, wherein the chaotropic substance is selected from the group consisting of urea, guanidinium hydrochloride and a thiocyanate, and wherein the protease treatment produces an active blood coagulation factor.

In addition, the present invention is directed to a method of proteolytically cleaving a proenzyme or proform of a blood coagulation factor, further comprising the step of immobilizing the proenzyme or proform on a solid carrier material prior to the incubation step. In such a method, the solid carrier material can be a slightly soluble salt or a chelate of a bivalent metal. A suitable bivalent metal is an alkaline earth metal.

The detergent used in these methods is selected from the group consisting of deoxycholate, dodecylsulfate, CHAPS, Brij® (polyethyleneglycolethers of lauryl-, cetyl-, stearyl- and oleyl-alcohols), Tween® (polyoxyethylene derivatives of sorbitanesters), Triton® (4-(1,1,3,3-tetramethylbutyl) phenol) and Pluronic® (polyalkylenglycols based on ethylene and propylene oxide). Moreover, the protease is selected from the group consisting of trypsin, chymotrypsin, plasmin, kallikrein, dispase, endoproteinase Glu-C, endoproteinase Lys-C and endoproteinase Asp-N.

A suitable proenzyme or proform of a blood coagulation factor for the claimed methods is selected from the group consisting of Factor V, Factor VII, Factor VIII, Factor IX, Factor X, Factor XI, Factor XII, Factor XIII and protein C.

The present invention also is directed to a method of activating a blood coagulation factor, comprising the steps of:

(a) providing a solution containing a proenzyme or proform of a blood coagulation factor;

(b) contacting the proenzyme-containing solution with a solid carrier to immobilize the proenzyme or proform on the carrier;

(c) treating the immobilized proenzyme or proform with a protease in the presence of a detergent or a chaotropic substance to obtain a solution that contains active blood coagulation factor;

(d) separating the carrier from the solution of step (c);

(e) isolating active blood coagulation factor from the solution of step (d); and (f) purifying the isolated active blood coagulation factor to homogeneity to obtain pure active blood coagulation factor.

A suitable proenzyme or proform of a blood coagulation factor for such a method is selected from the group consisting of Factor V, Factor VII, Factor VIII, Factor IX, Factor X, Factor XI, Factor XII, Factor XIII and protein C. Moreover, the solid carrier can be a slightly soluble salt or a chelate of a bivalent metal, such as an alkaline earth metal.

Such activation methods can be performed with a protease that is selected from the group consisting of trypsin, chymotrypsin, kallikrein, dispase, endoproteinase Glu-C, endoproteinase Lys-C and endoproteinase Asp-N. Furthermore, a suitable detergent is selected from the group consisting of deoxycholate, dodecylsulfate, CHAPS, Brij®, Tween®, Triton® and Pluronic®. In addition, the chaotropic substance is selected from the group consisting of urea, guanidinium hydrochloride and a thiocyanate.

The present invention is further directed to a method of producing a pharmaceutical composition containing an active blood coagulation factor, comprising the steps of:

(a) obtaining a purified preparation of active blood coagulation factor by the methods described above; and (b) combining the active blood coagulation factor with a pharmaceutically acceptable vehicle.

The present invention also includes pharmaceutical compositions comprising purified active blood coagulation factor obtained by the above-described methods and a pharmaceutically acceptable vehicle.

DETAILED DESCRIPTION

Figure 1:
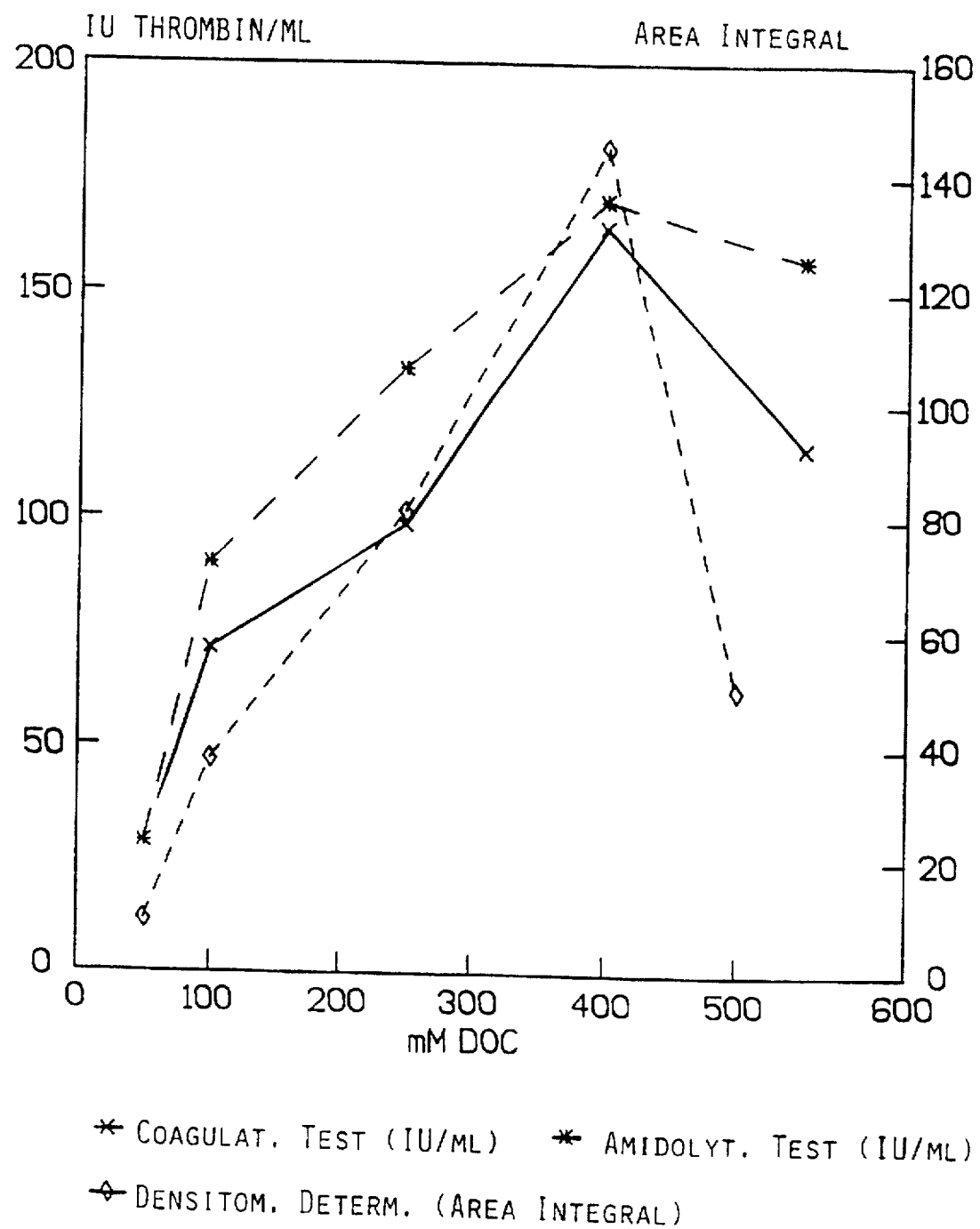
FIG. 1 shows the effect of deoxycholate (DOC) on the yield of active thrombin.

The methods described herein provide an improved approach for isolating certain fragments of proteins. These methods are particularly suited for preparing active blood coagulation factors from proenzymes or proform of a blood coagulation factor. Examples of blood coagulation factors that are proteolytically activated include prothrombin (Factor II), Factor V, Factor VII, Factor VIII, Factor IX, Factor X, Factor XI, Factor XII, Factor XIII and protein C. See, for example, Campbell et al., *Phil. Trans. R. Soc. Lond. B.* 332: 165 (1991), Hemker et al., *Haemostasis* 21: 189 (1991), and Kurachi, *Biotechnology* 19: 177 (1991). Although protein C plays an important role in the anticoagulant pathway, researchers have considered protein C to be a "coagulation factor." See, for example, Kurachi, *supra.* Accordingly, the term "blood coagulation factor," as used herein, includes protein C. In addition to such blood coagulation factors, the methods described herein can be used to prepare plasmin from plasminogen.

The present invention takes advantage of the discovery that the proteolytic cleavage of proteins, such as proenzymes or proforms, can be controlled if carried out in the presence of either a detergent or a chaotropic substance. As shown herein, the cleavage pattern of proteins varies according to the type and concentration of protease, detergent and chaotropic substance. This finding opens up the possibility of selecting the reaction environment such that only a few and precisely selected protein fragments are formed during proteolysis.

A plurality of proteases can be used to cleave proenzymes or proforms, including chymotrypsin, dispase, endopeptidase Arg-C, endoproteinase Lys-C, endoproteinase Glu-C, endoproteinase Asp-N, factor Xa, kallikrein, papain, pepsin, plasmin, pronase, proteinase K, staphylocoagulase, subtilisin, thrombin, trypsin (in particular, human, bovine, porcine), trypsin-like proteases from arthropods or microorganisms (e.g. *Streptomyces griseus*-trypsin), and serine-proteases from venomous snakes (such as *Angkistrodon rhodostoma, Bothrops atrox, Dispholidus typus, Echis carinatus, Naja nigrocollis, Oxyuranus scutellatus* scutellatus). Trypsin, chymotrypsin, kallikrein, dispase or the endoproteinase Glu-C, Lys-C or Asp-N, are preferably used as the protease. Such proteases can be isolated from natural sources or can be obtained by recombinant methodology.

In the presence of a detergent, a proenzyme can be cleaved so selectively that the desired enzyme product forms the dominant portion of the proteolytic digest. Suitable detergents include deoxycholate (DOC), dodecylsulfate (SDS), CHAPS and polyoxyethylene derivatives, such as Brij®, Tween®, Triton® and Pluronic®. DOC is a preferred detergent. In addition to controlling proteolysis, the presence of a detergent further facilitates the desorption of protein fragments from a solid carrier.

Suitable chaotropic substances include urea, guanidinium hydrochloride and thiocyanates. However, the chaotropic substance should not be a calcium salt if the substrate is a proenzyme or proform of the blood coagulation cascade. This is so because calcium salts are "coagulatively active" in the sense that they could activate the proenzymes. Accordingly, the inclusion of a calcium salt will cause a loss of control of proteolysis.

In a preferred variation of the present method, a proenzyme substrate is immobilized on a solid carrier material. This variation facilitates recovery of the active enzyme because the inactive portion of the proenzyme will remain adsorbed to the solid carrier, which can be separated from the reaction solution.

European patent application No. EP-A-0 378 798 describes a method in which copolymers are used as carriers for prothrombin.

As shown herein, it is possible to control the cleavage of a proenzyme that has been immobilized either on a solid carrier of a slightly soluble salt or as a chelate of a bivalent metal. Suitable salts include $Ca_3(PO_4)_2$, $CaSO_4$, $CaCo_3$, $BaSO_4$, $BaCO_3$ or barium citrate. For example, such salts can be added to a prothrombin-containing solution, or they may be formed in situ by precipitation of the salt in a prothrombin-containing solution. Preferably, the bivalent metal is an alkaline earth metal.

A particular advantage of using bivalent ions for the carrier is that they selectively bind proenzymes or proforms of certain blood coagulation factors via a gamma-carboxy-glutamic acid terminus. For example, proteolytic activation of prothrombin results in the formation of thrombin and a protein fragment that contains the gamma-carboxy-glutamic acid terminus. Consequently, newly-formed thrombin can be easily separated from the protein fragment which remains adsorbed to the bivalent ions of the carrier. Other blood coagulation factors that have a gamma-carboxy-glutamic acid terminus include Factor VII, Factor IX, Factor X and protein C.

Additional suitable carriers include hydroxylapatite, a hydroxylapatite gel or a metal chelate-affinity chromatographic carrier loaded with a bivalent cation (e.g. Pharmacia Chelating Sepharose®). See, generally, Woodward (ed.), IMMOBILIZED CELLS AND ENZYMES: A PRACTICAL APPROACH (IRL Press 1985).

Following proteolysis, the desired product in the reaction supernatant can be subjected to further purification steps. For example, gel permeation chromatography or affinity chromatography can be used to concentrate and to isolate the protein product. Preferably, affinity chromatography is used to obtain concentrated samples of the desired product. Dye ligand affinity chromatographic carriers with ligands of the Cibacron®-Blue F3GA-type (produced by Ciba Geigy) or Procion®-Red HE-3B (produced by ICI) or related dyes have proved to be suitable.

Proteins may be adsorbed on the respective affinity matrix (e.g. Fractogel® TSK AF-Blue (produced by Merck), Blue-Sepharose® CL-6B (produced by Pharmacia) in the batch or in the packed column directly from the desorption supernatant after the solid phase activation step. Subsequently, protein fragments are separated from detergent by washing with a buffer, and the product is eluted with a highly molar (e.g. 1M) chaotropic substance (e.g. KSCN or $NH_4SCN$).

The eluate may be freed from the chaotropic substance by gel permeation chromatography (e.g. via Sephadex® G25), diafiltration or dialysis. After reconstituting the protein product in a suitable buffer or a salt solution, the protein can be purified to homogeneity using well-known techniques such as reverse phase chromatography, affinity chromatography or gel permeation chromatography.

Examples 1–6 show that the method of the present invention can be used to obtain pure thrombin. Similarly, Example 7 demonstrates that pure, activated protein C can be prepared by the methods described herein. More generally, the present methods can be used to obtain purified, active blood coagulation factors for the preparation of pharmaceutical compositions.

Active blood coagulation factors can be formulated as pharmaceutical compositions according to known methods, whereby the purified, active factors are combined with a pharmaceutically acceptable vehicle. A composition is said to contain a "pharmaceutically acceptable vehicle" if its administration can be tolerated by a recipient patient. Sterile phosphate-buffered saline is one example of a pharmaceutically acceptable vehicle. Other suitable vehicles are well-known to those in the art. See, for example, REMINGTON'S PHARMACEUTICAL SCIENCES, 18th Ed. (1990).

For purposes of therapy, an active blood coagulation factor and a pharmaceutically acceptable vehicle are administered to a patient in a therapeutically effective amount. A pharmaceutical composition is said to be administered in a "therapeutically effective amount" if the amount administered is physiologically significant. An agent is physiologically significant if its presence results in a detectable change in the physiology of a recipient patient. In the present context, for example, a pharmaceutical composition comprising Factor V, Factor VII, Factor VIII, Factor IX, Factor X, Factor XI, Factor XII, or Factor XIII is physiologically significant if its presence enhances blood coagulation. In contrast, a pharmaceutical composition comprising protein C is physiologically significant if its presence inhibits blood coagulation.

A particular advantage of the presently described methods is that detergent treatment markedly inactivates any virus potentially present in a starting material that has been obtained from a virus-contaminated pool. In one case it was found that no vaccinia viruses were detectable in a thrombin preparation produced according to the method of the invention, although the starting material (a fermentation supernatant) had contained vaccinia. Those of skill in the art are aware that additional measures can be used to inactivate infectious agents in the starting material, such as vapor-heat treatment of a lyophilized product.

The present invention, thus generally described, will be understood more readily by reference to the following examples, which are provided by way of illustration and are not intended to be limiting of the present invention.

EXAMPLE 1

Effect of Detergent or Chaotropic Substance on the Tryptic Cleavage of Immobilized Prothrombin In these studies, samples of prothrombin were incubated with trypsin in the absence or presence of a detergent or a chaotropic substance. A cell culture supernatant medium containing recombinant human prothrombin was obtained as described in international application No. WO 91/11519. To immobilize prothrombin, an aliquot of the medium was mixed with five grams of powdered $Ca_3(PO_4)_2$ per 100 IU of prothrombin, and the mixture was slightly stirred at 4° C. for one hour. Subsequently, the solid phase of the mixture was pelleted by centrifuging at 5000 xg, the pellet was resuspended in 40 ml of 20 mM Tris-HCl buffer (pH 7.4), stirred for 10 minutes, and again the mixture was centrifuged at 5000 xg. This procedure was repeated once with Tris-HCl buffer that contained 40 ml of 5% (W/V) ammonium sulfate, and once again with 40 ml of Tris-HCl buffer without ammonium sulfate.

In the same manner, a partial prothrombin complex, e.g. a mixture of Factors II, IX and X, can be used as the prothrombin-containing starting material for preparing the immobilized prothrombin.

To determine the effect of chaotropic substances and detergents on the tryptic cleavage of prothrombin, the following four solutions were prepared:

Solution A: 20 mM Tris-HCl buffer (pH 8.3) with 0.5M urea,

Solution B: 20 mM Tris-HCl buffer (pH 8.3) with 0.05M sodium deoxycholate,

Solution C: 20 mM Tris-HCl buffer (pH 8.3) with 0.05M sodium dodecylsulfate, and Solution D: 20 mM Tris-HCl buffer (pH 8.3).

Two hundred milligrams of buffer-moist, washed prothrombin-containing pellet were added to one milliliter of each of the four solutions. After adding 20 µl of 20 mM Tris-HCl buffer with 1 mg/ml trypsin, the mixtures were shaken at room temperature. Aliquots of each mixture were removed after one, two and three hours, the solid phase of each aliquot was pelleted by centrifugation, and the supernatants were examined for protein fragment composition by Western blot analysis. The results were measured by densitometric scans of Western blots.

Table 1 shows the peak area integrals of the protein fragment bands at 12, 19, 23, 25.5, 33, 35 and 44 kD. The fragments at 33 kD and at 35 kD correspond to thrombin, with the 33 kD form representing active thrombin. In contrast to the three-hour incubation in pure Tris-HCl buffer (i.e. solution D), all solutions with a detergent or a chaotropic substance contained a majority of protein fragments that were greater than 30 kD. Even after three hours of incubation with trypsin, active thrombin was the major component in the sample that contained sodium deoxycholate (i.e., solution B).

These results demonstrate that tryptic cleavage produced fragments of different sizes, and that the amount of the various fragments varies according to the presence of a detergent or chaotropic substance.

TABLE 1

| Molecular Mass (kD) | | 12 | 19 | 23 | 25.5 | 33 | 35 | 44 |
|---|---|---|---|---|---|---|---|---|
| Solution | Reaction time (h) | | | Peak Area Integral: | | | | |
| A | 1 | 26 | 19 | 22 | 14 | 94 | 95 | |
| | 2 | 22 | 20 | 13 | | 54 | 20 | |
| | 3 | 24 | 27 | 14 | | 51 | 17 | |
| B | 1 | | | | 31 | 165 | 90 | |
| | 2 | 15 | | | | 175 | 25 | |
| | 3 | 18 | | | | 170 | | |
| C | 1 | | | | | | 53 | 11 |
| | 2 | | | | | | 35 | 2 |
| | 3 | | | | | | 9 | |
| D | 1 | 25 | | 132 | | 117 | 22 | |
| | 2 | 25 | | 120 | | 34 | | |
| | 3 | 42 | | 129 | | | | |

EXAMPLE 2

Cleavage of Immobilized Prothrombin by Various Proteases in the Presence of a Detergent An aliquot of a prothrombin-containing cell culture supernatant was treated with $Ca_3(PO_4)_2$, and immobilized prothrombin was washed with buffer.

Eight samples of 250 mg of buffer-moist adsorbate were each suspended in one milliliter of 20 mM Tris-HCl buffer (pH 8.3) containing 200 mM sodium deoxycholate. Fifty microliters of the following eight enzymes, dissolved in 20 mM Tris-HCl (pH 8.3) with 0.9% sodium chloride ("TBS"), were added to the one milliliter samples: 250 U/ml porcine pancreas kallikrein, 1 mg/ml *Bacillus polymyxa* dispase I, 350 U/ml bovine pancreas α-chymotrypsin, 0.76 mg/ml porcine pancreas trypsin, 1 mg/ml *Staphylococcus aureus*

V8 endoproteinase Glu-C, 0.1 mg/ml *Lysobacter enzymogenes* endoproteinase Lys-C, 0.04 mg/ml *Pseudomonas fragi* endoproteinase Asp-N, and 20 U/ml human Factor Xa.

The mixtures were incubated at room temperature with shaking for two hours with the exception of the kallikrein-containing solution which was incubated for 20 hours. After incubation, aliquots of the mixtures were mixed (1:1) with sodium dodecylsulfate sample buffer and examined for protein fragment composition by Western blot analysis.

Table 2 shows the peak area integrals of the fragment bands at 12, 18, 19, 20, 23, 33, 34, 35, 44, 47, 50, 52, 54, 55, 71 and 75 kD. The results demonstrate that a series of fragments in the molecule mass range of 12 to 71 kD can be produced by digestion with the above-mentioned proteases. The fragment corresponding to active thrombin (33 kD) can be obtained in a particularly high yield by tryptic cleavage of prothrombin.

with 0.1% trifluoroacetic acid in water (solvent A) on a reverse phase HPLC column (Nucleosil 100-5C18, 125×4 mm; flow rate: 1.7 ml/min). Protein fragments were eluted from the column with 0.1% trifluoroacetic acid in acetonitrile (solvent B) with a linear gradient of 30% to 70% acetonitrile over 30 minutes at a flow rate of 1.7 ml/min. Six main peaks were detected at 220 nm (retention times: 10.01 minutes; 11.96 minutes; 12.68 minutes; 13.47 minutes; 13.94 minutes; 14.47 minutes). The peaks were collected separately and lyophilized. The protein fragments were analyzed using SDS-PAGE with Coomassie staining, as well as by Western blot analysis with a polyclonal rabbit-anti-human prothrombin-antiserum. The molecular masses of the fragments in the six main peaks were determined to be 9 kD, 16 kD, 21 kD, 23 kD, 12 kD and 33 kD.

EXAMPLE 5
Recovery of Thrombin

Approximately 10 gm of a buffer-moist, prothrombin-containing pellet were resuspended in 50 ml of 0.76 mg/ml

TABLE 2

| Molecular Mass (kD) Protease | 12 | 18 | 19 | 20 | 23 | 33 | 34 | 35 | 44 | 47 | 50 | 52 | 54 | 55 | 71 | 75 |
|---|---|---|---|---|---|---|---|---|---|---|---|---|---|---|---|---|
| | | | | | | Peak Area Integral | | | | | | | | | | |
| Kallikrein | | 12 | 31 | | | | | | 15 | 16 | | 16 | | | | 59 |
| Dispase | | | | | | | | 36 | | 27 | 8 | 39 | | 18 | 44 | |
| α-Chymotrypsin | | | | | | | 7 | 57 | 9 | | | | 18 | 44 | | |
| Trypsin | 20 | | | | 14 | 56 | | | | | | | | | | |
| Endoproteinase Glu-C | | 13 | 28 | | | 39 | 17 | 13 | 17 | | | | 78 | | | |
| Endoproteinase Lys-C | | | | | | | | 6 | | 51 | | | | | | 21 |
| Endoproteinase Asp-N | | | | | | 21 | | 83 | 11 | | | | 11 | | | 19 |
| Factor Xa | | | | | | | 12 | 10 | | | | | 31 | | | 98 |

EXAMPLE 3

Cleavage of Immobilized Prothrombin in the Presence of Various Concentrations of Deoxycholate A pellet containing recombinant prothrombin immobilized on $Ca_3(PO_4)_2$ was obtained from a prothrombin-containing cell culture, as described above. Five 0.6 gram samples of moist adsorbate were suspended in 3 ml of 20 mM Tris-HCl buffer (pH 8.3) containing 50 mM, 100 mM, 250 mM, 350 mM or 500 mM sodium deoxycholate. Sixty microliter aliquots of 0.76 mg/ml trypsin were added to each sample, and the mixtures were incubated for three hours at room temperature with shaking. After incubation, the buffers of the samples were changed against 0.9% NaCl.

Samples were examined for thrombin activity using normal plasma in a coagulation test and in an amidolytic assay. Amidolytic activity was determined photometrically with the chromogenic substrate TH-1 (2 AcOH.-D-CHG-ala-arg-p-nitroanilide) against an international thrombin standard. FIG. 1 shows that the maximum yield of active thrombin (i.e., 33 kD-fragment) was obtained with 350 mM sodium deoxycholate. Active thrombin was not further degraded by trypsin during an incubation of at least 20 hours.

EXAMPLE 4

Purification of Protein Fragments of Cleaved Prothrombin

One and one-half milliliters of the prothrombin fragment-containing solution obtained in Example 3 were adsorbed porcine trypsin (Sigma T-0134) in 20 mM Tris-HCl buffer (pH 8.3) which contained 200 mM sodium deoxycholate. The suspension was incubated for one hour at room temperature with slight stirring. After incubation, calcium phosphate was separated by centrifugation. The supernatant was found to contain primarily thrombin and a few other prothrombin fragments.

Thrombin was purified from the supernatant using column chromatography. A column having a cross-sectional area of 8 $cm^2$ was packed with Fractogel® TSK-AF Blue (Merck) at a height of 12 mm (gel volume~9.6 ml) in 20 mM Tris-HCl buffer (pH 8.3) and washed with the same buffer. These and all subsequent steps were performed at 4° C.

The thrombin-containing supernatant (approximately 50 ml) was pumped over the gel at a flow rate of 2 ml/min to effect adsorption. Thereafter, nonspecifically bound prothrombin fragments were eluted with 20 ml of 0.5M sodium chloride solution, 40 ml of 1.0M sodium chloride solution and 20 ml of 20 mM Tris-HCl buffer (pH 7.4) at a flow rate of 6 ml/min. In reverse flow direction, prothrombin fragments were then eluted at 1 ml/min with 20 mM Tris-HCl buffer which contained 1M KSCN. The eluate was photometrically measured at 280 nm with a flow cell, and a total of 15 ml was collected.

Figure 2:
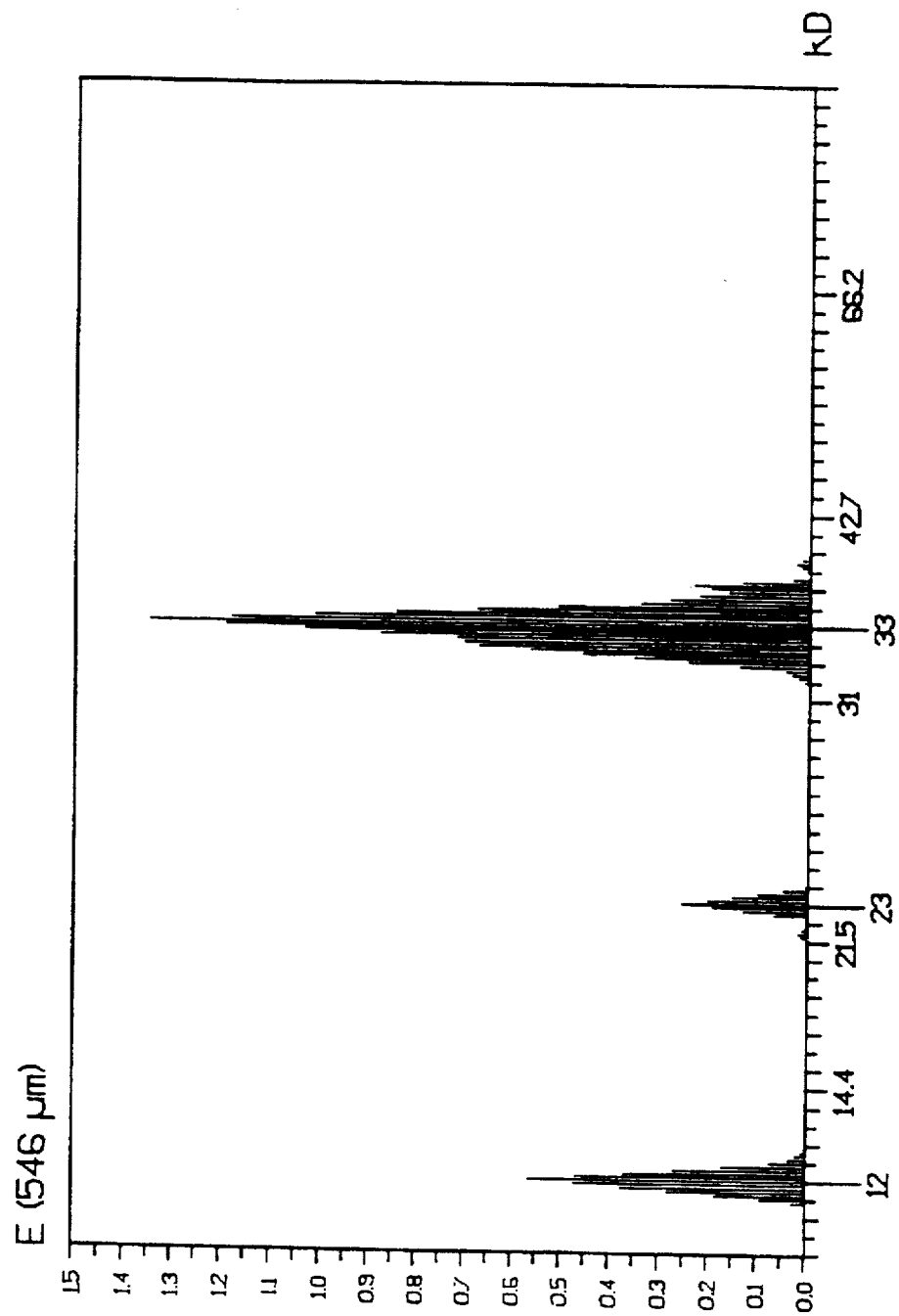
FIG. 2 shows the fragment composition of a peptide digest produced by treatment of prothrombin with trypsin in the presence of deoxycholate.

The protein content of the eluate was 188 mg/ml according to the method of Bradford. FIG. 2 shows the fragment composition, as determined by densitometric scan of a Western blot. About 30% of recovered protein was thrombin, and the dominant portion was the 33 kD fragment of active thrombin. The thrombin had a specific activity of approximately 2200 IU/mg protein, as determined by a thrombin time assay. Thus, approximately 100 IU of thrombin were obtained from 1 IU of prothrombin by tryptic solid phase activation.

The thrombin-containing solution obtained by the present methods can be further purified in a known manner, concentrated and processed to a pharmaceutical composition.

EXAMPLE 6

Cleavage of Dissolved Prothrombin

Two 1 ml samples of a prothrombin-containing fermentation supernatant were mixed with 1 ml of 40 mM Tris-HCl buffer (pH 8.3) which contained either 0.1M sodium deoxycholate or 0.1M sodium dodecylsulfate. The final concentration of either detergent was 0.05M. For comparison, a third 1 ml sample of prothrombin-containing fermentation supernatant was mixed with 40 mM Tris-HCl buffer that did not contain a detergent. Fifteen milliliters of a solution containing 1 mg trypsin/ml in 20 mM Tris-HCl buffer (pH 8.3) with 0.9% NaCl were added to each sample, and the mixtures were incubated at room temperature for four hours with shaking.

After one, two, three and four hours, 50 µl aliquots of each sample were diluted with Laemmli buffer (1:1), boiled and fractionated using a 12% sodium dodecylsulfate-polyacrylamide gel. Western blot analysis was performed using anti-human-factor II rabbit serum as the first antibody and goat-anti-rabbit IgG peroxidase conjugate as the second antibody. Western blots were developed with 4-chloro-1-naphthol, and densitometrically examined in the impinging light. The results are shown in Table 3.

TABLE 3

| Addition | Reaction Time (h) | Molecular mass (kD) 19 | 25.5 | 33 | 35 |
|---|---|---|---|---|---|
|  |  | Peak Area Integral |  |  |  |
| Deoxycholate | 1 |  |  | 10 |  |
|  | 2 |  |  | 9 |  |
|  | 3 |  |  | 7 |  |
|  | 4 |  |  | 6 |  |
| Dodecylsulfate | 1 | 8 |  |  | 68 |
|  | 2 | 6 |  |  | 67 |
|  | 3 | 5 |  |  | 69 |
|  | 4 | 4 |  |  | 67 |
| Blank Value | 1 |  | 4 | 9 | 4 |
|  | 2 |  | 3 | 1 | 0 |
|  | 3 |  | 0 | 0 | 0 |

EXAMPLE 7

Activation of Protein C

The activation of human protein C by the proteolytic enzyme, plasmin, is difficult to control. See, for example, Bajaj et al., *Prep. Biochem.* 13: 191 (1983). Plasmin initially activates, and then, degrades protein C. An experiment was performed to determined whether the activation process could be controlled with detergent.

In this study, a solution of protein C was prepared at a concentration of 9 U/ml in 20 mM Tris-buffered saline (pH 7.35). After adding plasmin to a final concentration of 1.25 nM, the mixture was incubated at 37° C. Samples were removed from the incubation mixture at various times and were diluted ten-fold with 20 mM Tris-buffered saline (pH 7.35).

The extent of plasmin-induced activation of protein C was determined by measuring the prolongation of clotting time in the activated partial thromboplastin time (APTT) assay of Dahlbäck et al., *Proc. Nat'l Acad. Sci. USA* 90: 1004 (1993). Briefly, 50 µl of APTT reagent (APTT-Automated or Platelin LS [Organon Tecknika]) was incubated with an equal volume of normal human plasma for five minutes at 37° C. The coagulation reaction was initiated by the addition of 100 µl of a mixture containing 50 µl of 10 mM Tris-HCl, 50 mM NaCl, 30 mM CaCl$_2$ (pH 7.5) and 50 µl of test sample. Incubations were performed either in the absence or in the presence of 0.1M sodium dodecylsulfate. The anticoagulant activity of activated protein C was determined by the extent of prolongation of APTT in relation to the starting level.

Figure 3:
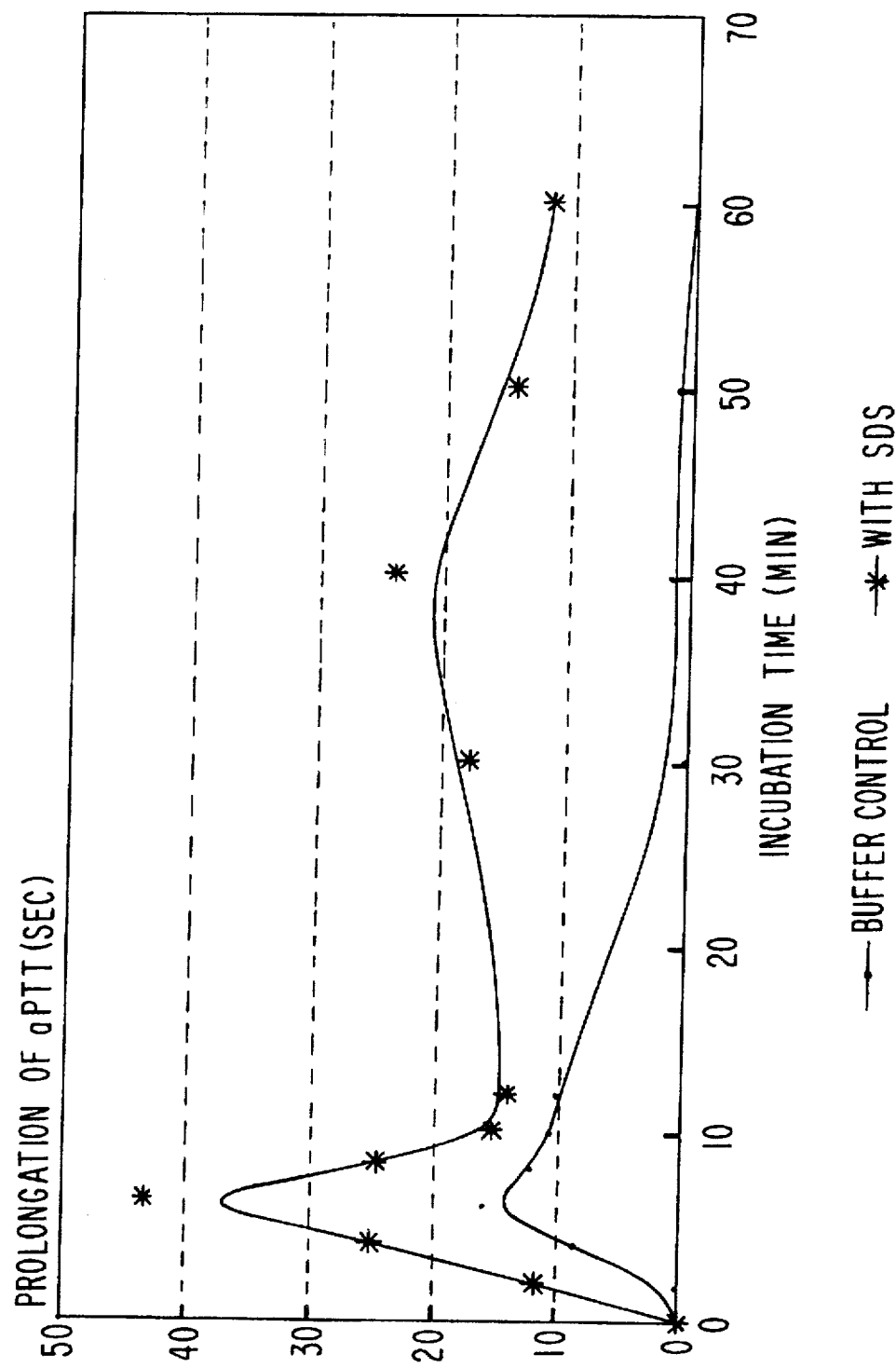
FIG. 3 shows the effect of sodium dodecylsulfate on the activation of protein C by plasmin.

As shown in FIG. 3, treatment of protein C with plasmin in the absence of sodium dodecylsulfate resulted in an initial activation of protein C, followed by inactivation of protein C after 30 minutes. In contrast, samples incubated in the presence of sodium dodecylsulfate contained anticoagulant activity even after a 60 minute incubation. Thus, the methods described herein can be used to control the activation of protein C.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

What is claimed is:

1. A method of proteolytically cleaving a proenzyme or proform of a blood factor selected from the group consisting of Factor Va, Factor VIIa, Factor VIIIa, Factor IXa, Factor Xa, Factor XIa, Factor XIIa, Factor XIIIa and activated protein C, comprising the step of incubating said proenzyme or proform with a protease in the presence of a detergent or a chaotropic substance, wherein (i) said chaotropic substance is selected from the group consisting of urea, guanidinium hydrochloride and a thiocyanate; (ii) said detergent is selected from the group consisting of deoxycholate, dodecylsulfate, CHAPS, polyethyleneglycolethers of lauryl-, cetyl-, stearyl- and oleyl-alcohols, polyexyethylene derivatives of sorbitanesters, 4-(1,1,3,3 -tetramethylbuthyl) phenol, and polyalkylenglycols based on ethylene and propylene oxide; and (iii) said incubating produces an active blood factor.

2. The method of claim 1, further comprising the step of immobilizing said proenzyme or proform on a solid carrier material prior to said incubation step.

3. The method of claim 2, wherein said solid carrier material is a slightly soluble salt or a chelate of a bivalent metal.

4. The method of claim 3, wherein said bivalent metal is an alkaline earth metal.

5. The method of claim 1, wherein said protease is selected from the group consisting of trypsin, chymotrypsin, plasmin, kallikrein, dispase, endoproteinase Glu-C, endoproteinase Lys-C and endoproteinase Asp-N.

6. A method of obtaining a purified activated blood factor selected from the group consisting of Factor Va, Factor VIIa, Factor VIIIa, Factor IXa, Factor Xa, Factor XIa, Factor XIIa, Factor XIIIa and activated protein C, comprising the steps of:

(a) providing a solution containing a proenzyme or proform of the activated blood factor;

(b) contacting said proenzyme- or proform-containing solution with a solid carrier to immobilize said proenzyme or proform on said carrier;

(c) treating said immobilized proenzyme or proform with a protease in the presence of a detergent or a chaotropic substance to obtain a solution that contains activated blood factor;

(d) separating said carrier from said solution of step (c);

(e) isolating activated blood factor from said solution of step (d); and (f) purifying said isolated activated blood factor to homogeneity to obtain pure activated blood factor.

7. The method of claim 6, wherein said solid carrier is a slightly soluble salt or a chelate of a bivalent metal.

8. The method of claim 7, wherein said bivalent metal is an alkaline earth metal.

9. The method of claim 6, wherein said protease is selected from the group consisting of trypsin, chymotrypsin, kallikrein, dispase, endoproteinase Glu-C, endoproteinase Lys-C and endoproteinase Asp-N.

10. The method of claim 9, wherein said detergent is selected from the group consisting of deoxycholate, dodecylsulfate; CHAPS; polyethleneglycolethers of lauryl-, cetyl-, stearyl- and oleyl-alcohols; polyexyethylene derivatives of sorbitanesters; 4-(1,1,3,3-tetramethylbuthyl) phenol; and polyalkylenglycols based on ethylene and propylene oxide.

11. The method of claim 9, wherein said chaotropic substance is selected from the group consisting of urea, guanidinium hydrochloride and a thiocyanate.

12. A method of producing a pharmaceutical composition containing an activated blood factor selected from the group consisting of Factor Va, Factor VIIa, Factor VIIIa, Factor IXa, Factor Xa, Factor XIa, Factor XIIa, Factor XIIIa and activated protein C, comprising the steps of:

(a) obtaining a purified preparation of activated blood factor by the method of
  (i) providing a solution containing a proenzyme or proform of the activated blood factor;
  (ii) contacting said solution with a solid carrier to immobilize said proenzyme or proform on said carrier;
  (iii) treating said immobilized proenzyme or proform with a protease in the presence of a detergent or a chaotropic substance to obtain a solution that contains activated blood factor;
  (iv) separating said carrier from said solution of step (iii);
  (v) isolating activated blood factor from said solution of step (iv); and
  (vi) purifying said isolated activated blood factor to homogeneity to obtain purified activated blood factor; and (b) combining said purified activated blood factor with a pharmaceutically acceptable vehicle.

13. A pharmaceutical composition comprising (a) purified activated blood factor selected from the group consisting of Factor Va, Factor VIa, Factor VIIIa, Factor IXa, Factor Xa, Factor XIa, Factor XIIa, Factor XIIIa and activated protein C obtained by the method of
  (i) providing a solution containing a proenzyme or proform of the activated blood factor;
  (ii) contacting said solution with a solid carrier to immobilize said proenzyme or proform on said carrier;
  (iii) treating said immobilized proenzyme or proform with a protease in the presence of a detergent or a chaotropic substance to obtain a solution that contains activated blood factor;
  (iv) separating said carrier from said solution of step (iii);
  (v) isolating activated blood factor from said solution of step (iv); and
  (vi) purifying said isolated activated blood factor to homogeneity to obtain purified activated blood factor, and (b) a pharmaceutically acceptable vehicle.

* * * * *